United States Patent [19]

Keeth

[11] 4,362,157
[45] Dec. 7, 1982

[54] TEMPLATE FOR LOCATING HYPODERMIC INJECTION SITES

[76] Inventor: John D. Keeth, 1416 Naperville Rd., Wheaton, Ill. 60187

[21] Appl. No.: 235,768

[22] Filed: Feb. 18, 1981

[51] Int. Cl.³ .............................................. A61M 5/00
[52] U.S. Cl. ................................................. 128/215
[58] Field of Search ................ 128/215, 213, 316, 1 R

[56] References Cited

U.S. PATENT DOCUMENTS

| | | | |
|---|---|---|---|
| 2,245,350 | 6/1941 | Marshall | 128/215 X |
| 2,814,294 | 11/1957 | Figge | 128/215 |
| 3,542,022 | 11/1970 | Bartnik | 128/215 |
| 3,547,121 | 12/1970 | Cherry | 128/215 |
| 4,228,796 | 10/1980 | Gardiner | 128/215 |

FOREIGN PATENT DOCUMENTS

WO80/00060  1/1980  PCT Int'l Appl. ................. 128/215

Primary Examiner—Dalton L. Truluck
Attorney, Agent, or Firm—Thomas W. Speckman

[57] ABSTRACT

A template for identifying a set of sites on the skin for hypodermic injection and repeatedly locating unused sites in the set of sites and locating sites which have recently received an injection has at least one sheet which has a plurality of orifices at predetermined spaced sites corresponding to the set of skin sites, and a layer of liquid permeable absorbent material covering the orifices. The layer may be needle penetrable or both liquid and needle penetrable, if preferred. A second sheet having orifices corresponding to the orifices in the first sheet may be secured to the first sheet and the layer so that the orifices of the sheets are aligned with the layer between the sheets. In an alternative embodiment, bubbles containing an antiseptic liquid may be formed between the sheets, eliminating the layer of material between the sheets. The bubbles identify the shot sites. The template may be used to identify a set of sites on the skin for hypodermic injection and repeatedly locate the sites by using the hand to align the template, or aligning a portion of the template with a particular portion of the body. In this manner, the orifices or bubbles on the template are repeatedly aligned with the same set of skin sites. Orifices may be marked with a dye as they are used for injections, or the layer of material may be removed at each orifice as it is used. Bubbles may be punctured as they are used to identify shot sites.

19 Claims, 5 Drawing Figures

TEMPLATE FOR LOCATING HYPODERMIC INJECTION SITES

BACKGROUND OF THE INVENTION

This invention relates to templates for identifying hypodermic injection sites on the body, and more particularly to templates for repeatedly locating unused injection sites and determining which of the sites have recently received an injection.

Persons afflicted with diabetes, allergies and the like must receive a hypodermic injection of medicine daily, or at some other regular interval. Only certain parts of the body may be safely used for such injections without excessive discomfort or an inordinate risk of penetrating major veins or arteries. The parts generally used are on the thighs, the buttocks, the backs of each shoulder, and portions of the lower abdomen. Each of these body parts has an area known as a shot area, or shot range, in which a plurality of shot sites for hypodermic injection may be identified. Each shot range is about four inches square, and may include up to about thirty shot sites.

Each hypodermic injection insults the body tissue and adjacent muscle at the point of injection. It may take up to six months for the skin and muscle at the injection site to completely heal. If another shot is injected into the site before it is healed, a hard spot or knot will develop at the site as a result of the additional shot. Hardening may develop which makes the skin leathery, and it may be difficult to insert a needle in that site at a later time because the hardening caused by the double wound remains after the wound heals. Also, the process of osmosis by which the injected drugs enter the bloodstream may be inhibited if the site is not healed completely when it receives an additional shot.

It is difficult for a patient to determine which shot sites have recently received an injection because the wounds caused by the injections heal quickly at the surface of the skin. Also, the patient does not know that the site has been used recently until after the second shot is injected, when a knot develops at the site. As a result, it is not unusual for a patient to make many double injections and have several painful knots at any one time.

Physicians often suggest that patients locate unused injection sites by placing their hand against a particular point on the body, putting their thumb and fingers in a particular configuration, and making successive injections across from the thumb and adjacent fingers on succeeding days. For example, the base of the thumb may be butted against the hip bone, and the fingers may be directed across a line which is perpendicular to a line intersecting the center of the knee and the hip bone. Shots may be injected across from the thmb and adjacent fingers on succeeding days. After five days, the thumb and fingers may be moved forward toward the knee to another row for injections on succeeding days, and so forth, until the shot range of the thigh is used. The patient may then use the shot range on the other thigh, a buttock, back of a shoulder or lower abdomen. The first thigh should not be ued for injections again for about 180 days. This method of determining which sites have not recently received an injection is accurate, but does not identify previously used shot sites, and requires the patient to use adjacent shot sites most of the time. The patient may forget which shot sites have been used and inadvertently make an additional injection in a previously used site. Also, the patient cannot increase the distance between shots on succeeding days without great difficulty and inevitable errors.

A mechanical device has been developed which may be used to locate a previously used general portion of the body for additional injections, as described in U.S. Pat. No. 3,542,022, and other devices have been suggested which locate injection sites corresponding to particular internal organs or a fetus, as described in U.S. Pat. Nos. 3,547,121 and 2,245,350. However, none of the devices described in the patents just identified may be used to identify a set of sites in a shot range for hypodermic injection and repeatedly locate sites which have not recently received an injection by identifying used and unused shot sites in the shot range. Thus, there is a need for a device which identifies such a set of sites and repeatedly locates unused sites on the skin in the set of sites for hypodermic injection.

Accordingly, an object of this invention is to provide a template which accurately identifies a set of sites in a shot range for hypodermic injection, and repeatedly locates unused sites in the set of sites for injections on succeeding days.

Another object is to provide a template which enables the user to increase the distance between shots on succeeding days.

Yet another object is to provide such a template which is relatively inexpensive and may be discarded after use.

SUMMARY OF THE INVENTION

In keeping with one aspect of this invention, a template for identifying a set of sites on the skin for hypodermic injection and repeatedly locating unused sites in the set of sites and locating sites which have recently received an injection has at least one sheet which has a plurality of orifices at predetermined spaced sites corresponding to the set of skin sites, and a layer of liquid permeable absorbent material covering the orifices. The layer may be needle penetrable or both liquid and needle penetrable, if preferred. A second sheet having orifices corresponding to the orifices in the first sheet may be secured to the first sheet and the layer so that the orifices of the sheets are aligned and the layer is between the sheets. In an alternate embodiment, bubbles containing an antiseptic liquid may be formed between the sheets, eliminating the layer of material between the sheets. The bubbles identify the shot sites. The template may be used to identify a set of sites on the skin for hypodermic injection and repeatedly locate the sites by using the hand to align the template, or aligning a portion of the template with a particular portion of the body. In this manner, the orifices or bubbles on the template are repeatedly aligned with the same set of skin sites. Orifices may be marked with a dye as they are used for injections, or the layer of material may be removed at each orifice as it is used. Bubbles may be punctured as they are used to identify shot sites.

BRIEF DESCRIPTION OF THE DRAWINGS

The above mentioned and other features of this invention and the manner of obtaining them will become more apparent, and the invention itself will be best understood by reference to the following description of an embodiment of the invention taken in conjunction with the accompanying drawings in which.

DESCRIPTION OF THE PREFERRED EMBODIMENTS

Figure 1:
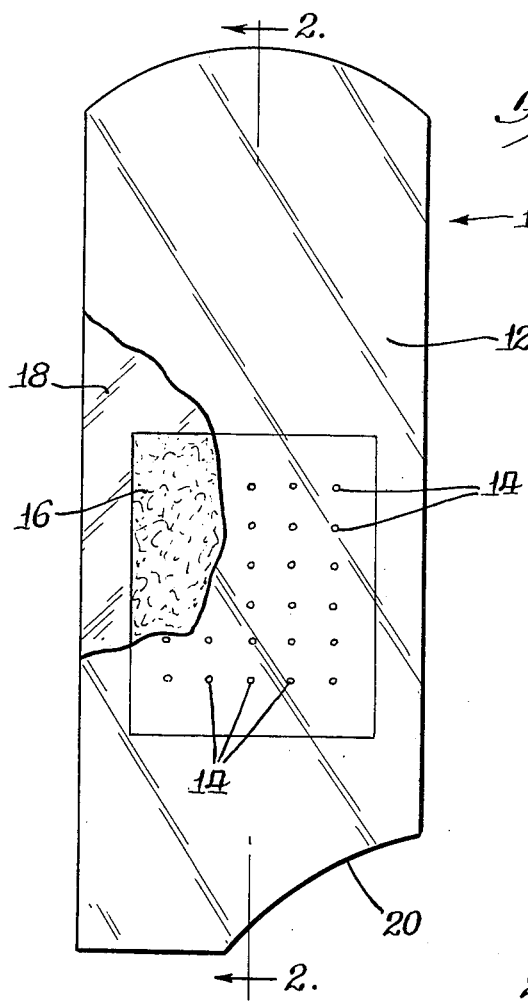
FIG. 1 is a front view of one embodiment of a template made according to this invention.
Figure 2:
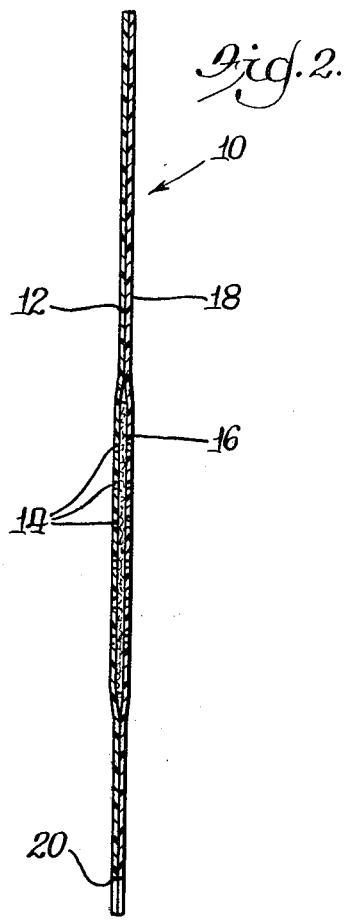
FIG. 2 is a sectional view of the template of FIG. 1 taken along line 2—2.

As seen in FIG. 1, a template 10 has a first sheet 12 having a plurality of means for identifying and marking sites on the skin for hypodermic injection, such as orifices 14, at predetermined spaced sites on the sheet. A layer 16 of liquid permeable absorbent material or needle penetrable material is secured to sheet 12 and covers the orifices 14. Layer 16 may be a single piece, as in FIG. 1, or it may be several pieces or strips, if preferred. Layer 16 may also be sandwiched between sheet 12 and a second sheet 18, if desired. If second sheet 18 is used, as in FIG. 1, the layer 16 need not be secured to the sheet 12. Sheet 18 includes orifices 14 which are aligned with the orifices in sheet 12 when the sheets are secured together.

Sheets 12, 18 may be made of any suitable material, such as transparent flexible plastic sheets about 0.005–0.008 inches thick. A single sheet of plastic may be folded over upon itself to form two sheets, if desired.

Layer 16 may be gauze or any other liquid penetrable or needle penetrable material. It may also be penetrable by both a needle and liquid. The layer 16 should absorb liquid liberally, but not so much that the liquid flows to an adjacent orifice 14. Layer 16 may have openings which correspond to orifices 14, provided that the openings are somewhat smaller than the orifices 14 so that the layer material may be marked in some way as the orifices 14 are used.

Figure 5:
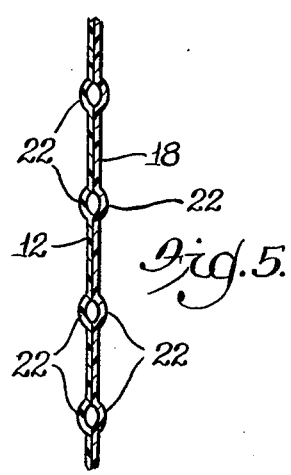
FIG. 5 is a partial sectional view of an alternate embodiment of the template of FIG. 1.

Layer 16 may be eliminated by forming bubbles 22 between the sheets 12, 18 corresponding to orifices 14, as seen in FIG. 5. The bubbles 22 identify and mark the sites for injection, and may be filled with a disinfectant or antiseptic liquid such as Mercurochrome, alcohol or the like. The plastic of the bubbles may be any suitable thickness which is needle penetrable.

Figure 3:
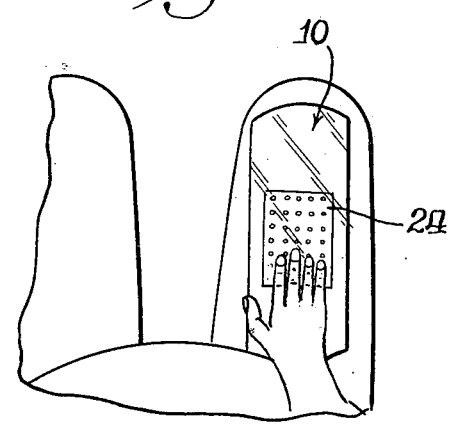
FIG. 3 is a plan view of the template of FIG. 1 in place on the right thigh of a user of the template.
Figure 4:
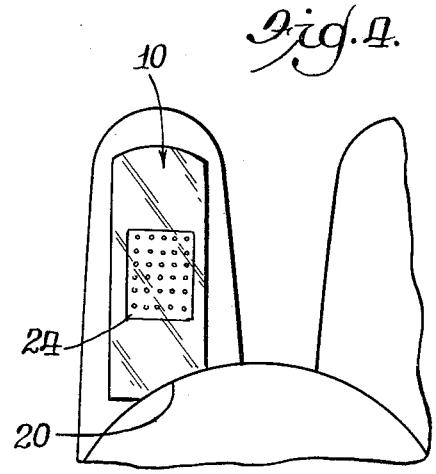
FIG. 4 is another plan view of the template of FIG. 1 in use on the left thigh of a user of the template.

The template 10 may take various shapes and may be many sizes. It may be square or rectangular, or may follow the contour of the knee or some other part of the body. A notch 20 may be provided in one corner of the template 10, as seen in FIGS. 1 and 4, or in other portions of the template 10, if desired. The notch 20 provides a surface against which the hip bone or other bone of the user may be placed to align the template 10 with a shot range 24 on the thigh, as seen in FIG. 4, or other area of the user's body. A shot range is an area on the body from which a set of sites on the skin may be identified for hypodermic injection. Commonly used shot ranges include an area on top of each thigh, as seen in FIGS. 3 and 4, an area on each buttock, an area behind each shoulder, and certain areas on the lower abdomen. Each shot range may be about 3 to 4 inches square, depending on the area of the body and size of the individual user. It is contemplated that up to about thirty shot sites may be identified in each shot range, so that one template will last about one month, but the set of sites could include more or fewer sites, if desired.

In one template actually made, the width of the template was about 5½ inches and the overall length of the template was about 15 inches. Thirty orifices 14 about 3/16 inches in diameter were provided in six rows, each row having five orifices. Both the rows of orifices and the orifices in each row were spaced about ⅝ inches apart between centers. The distance between the orifices 14 may vary depending on the physical size of the user. The distance may be increased for large persons, and may be decreased somewhat for relatively small persons.

Another template actually made was about 5½ inches wide and about 6¼ inches long. The number and configuration of orifices was the same as that used in the other template described.

In use, the template 10 is placed over an area of the body so that the orifices 14 cover a shot range 24, as seen in FIGS. 3 and 4. The orifices 14 determine the location of the set of sites on the skin which will receive an injection. The template 10 should be placed over the area by a known method or means so that the orifices 14 may be located over the same set of skin sites at a later time by the same method or means.

Orifices 14 may be repeatedly located over the same set of skin sites by various means. In FIG. 3, the hand of the user is placed in a known relationship to a bone which is adjacent the shot range, and the fingers are held in a known configuration. One row of orifices 14 is aligned with the fingers, to properly locate the orifices 14 over the shot range 24. For example, the base of the thumb may be butted against the hip bone. The orifice 14 in the corner adjacent the smallest finger may be placed adjacent that finger, and the other orifices 14 may be aligned with the line extending between the hip bone and the center of the knee.

In FIG. 4, the notch 20 is placed against a bone such as the hip bone and the orifices 14 may be aligned with the line extending between the hip bone and the center of the knee to repeatedly align the orifices 14 with the same set of skin sites in the shot range 24.

When the template 10 is properly aligned over a shot range 24, a colored antiseptic dye such as Mercurochrome may be placed on a site which is selected for injection. The dye is absorbed by the layer 16, permanently marking the orifice 14, and sterilizing the skin in preparation for the injection. If layer 16 is gauze, the needle may be injected into the skin through the gauze, or the template 10 may be removed and the needle injected directly into the skin. The discoloration produced by the dye will make the skin site visible.

When another injection is required, the orifices 14 may be located over the same set of skin sites, and another orifice 14 may be selected for injection. Used orifices may be easily identified by the dye, and unused orifices may be easily selected.

Unused sites may also be identified by removing the gauze in the orifice 14 after it is used. This may be accomplished with the needle, or any other suitable means.

The embodiment shown in FIG. 5 may be placed over a shot range by the methods and means described. Bubbles 22 may be penetrated with the needle, which makes used and unused skin sites easily identifiable. The disinfectant in the unused site is released onto the injection site as the needle penetrates the orifice 14 and enters the skin.

By identifying all of the potential injection sites with the template each time the template is placed on a shot range, the user may increase the distance between subsequent shots by selecting an unused site adequately distant from the last shot location within the shot range 24. This reduces discomfort and enables the wound to better heal. When all of the orifices 14 have been used, the template may be discarded.

The many advantages of this invention are now self-apparent. The template may be used to identify a set of sites in a shot range and repeatedly locate unused sites in the set for hypodermic injection. Sites which have recently received an injection may be easily and accurately identified, so that the user does not make a second injection in a skin site before the initial wound is healed, and successive sites may be distant from each other. The template is inexpensive, and may be discarded after use.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A template for identifying a set of skin sites in a shot range for hypodermic injection and repeatedly locating unused sites in the set of sites for succeeding injections comprising:
   a first flexible sheet having a plurality of orifice marking means at predetermined spaced intervals on said sheet corresponding to and identifying said set of skin sites;
   a flexible layer of liquid permeable absorbent material having a plurality of orifices aligned with said orifice marking means and capable of absorbing a coloring dye and retaining said coloring covering said marking means; and
   means for locating said template on a particular portion of the skin so that said marking means are repeatedly aligned with said set of skin sites.

2. A template for identifying a set of skin sites in a hot range for hypodermic injection and repeatedly locating unused sites in the set of sites for succeeding injections comprising:
   a first flexible sheet having a plurality of orifice marking means at predetermined spaced intervals on said sheet corresponding to and identifying said set of skin sites;
   a flexible layer of needle penetrable material covering said marking means and capable of absorbing a coloring dye and retaining said coloring; and
   means for locating said template on a particular portion of the skin so that said marking means are repeatedly aligned with said set of skin sites.

3. The template of claim 1 or 2 comprising a second sheet secured to said first sheet over said layer, said second sheet having orifice marking means aligned with said first sheet orifice marking means.

4. The template of claim 3 wherein said second sheet is formed by folding a continuous extension of said first sheet over upon itself.

5. The template of claim 3 wherein said first and second sheets are transparent plastic.

6. The template of claims 1 or 2 wherein said first sheet is transparent plastic.

7. The template of claims 1 or 2 wherein said layer is gauze.

8. The template of claims 1 or 2 wherein said layer comprises a plurality of pieces of material which cover said marking means.

9. The template of claims 1 or 2 comprising thirty marking means.

10. The template of claim 9 wherein said marking means are arranged on said template in six rows, each row having five marking means.

11. The template of claims 1 or 2 wherein the center of each of said marking means is about ⅝ inch from the center of the nearest adjacent marking means.

12. The template of claims 1 or 2 wherein said locating means comprises a notch in said template which communicates with a particular point on the body.

13. A template for identifying a set of skin sites in a shot range for hypodermic injection and repeatedly locating unused sites in the set of sites for succeeding injections comprising:
    a first sheet;
    a second sheet secured to said first sheet;
    a plurality of needle penetrable bubbles between said sheets at predetermined spaced intervals corresponding to said set of skin sites, said bubbles containing disinfectant; and
    means for locating said template on a particular portion of the skin so that said bubbles are repeatedly aligned with said set of skin sites.

14. The template of claim 13 wherein said second sheet is formed by folding said first sheet over upon itself.

15. The template of claim 13 wherein said first and second sheets are transparent plastic.

16. The template of claim 13 comprising thirty bubbles.

17. The template of claim 13 wherein said bubbles are arranged on said template in six rows, each row having five orifices.

18. The template of claim 13 wherein the center of each of said bubbles is about ⅝ inch from the center of the nearest adjacent bubble.

19. The template of claim 13 wherein said locating means comprises a notch in said template which communicates with a particular point on the body.

* * * * *